US009554589B2

(12) United States Patent
Varshney et al.

(10) Patent No.: US 9,554,589 B2
(45) Date of Patent: *Jan. 31, 2017

(54) FOOD STEGANOGRAPHY

(71) Applicant: INTERNATIONAL BUSINESS MACHINES CORPORATION, Armonk, NY (US)

(72) Inventors: Kush R. Varshney, Ossining, NY (US); Lav R. Varshney, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/155,828

(22) Filed: May 16, 2016

(65) Prior Publication Data

US 2016/0262437 A1 Sep. 15, 2016

Related U.S. Application Data

(63) Continuation of application No. 14/011,421, filed on Aug. 27, 2013.

(51) Int. Cl.
*G01N 7/00* (2006.01)
*A23L 1/30* (2006.01)
*G01N 30/86* (2006.01)

(52) U.S. Cl.
CPC .......... *A23L 1/30* (2013.01); *G01N 30/8651* (2013.01); *A23V 2002/00* (2013.01)

(58) Field of Classification Search
CPC ........ G01N 7/14; G01N 1/24; G01N 33/0031; G01N 3/12; A23L 1/22

(Continued)

(56) References Cited

U.S. PATENT DOCUMENTS 5,303,846 A * 4/1994 Shannon .............. B67D 1/0036
   222/129.4
5,783,544 A * 7/1998 Trinh ........................ A61L 9/14
   252/8.61

(Continued)

FOREIGN PATENT DOCUMENTS

EP 1389047 B1 7/2009
WO 2013/035070 A1 3/2013

OTHER PUBLICATIONS

Puiu, T., "White Smell: The Neutral Fragrance Discovered by Scientist", ZME Science, Nov. 28, 2012. Obtained at http://www.zmescience.com/research/studies/white-smell-neutral-smell-discovered-0424./ on Jun. 7, 2016, 2 pages.

(Continued)

*Primary Examiner* — Lisa Caputo
*Assistant Examiner* — Nigel Plumb
(74) *Attorney, Agent, or Firm* — Louis Percello

(57) ABSTRACT

The present disclosure relates to methods and systems for calculating a food additive. A first method includes identifying chemical compounds of an averse food ingredient, identifying chemical compounds of a flavorful food ingredient and calculating a set of chemical compounds for the food additive such that an olfactory perception of a mixture of the averse food ingredient, the flavorful food ingredient and the food additive is the same as an olfactory perception of only the flavorful food ingredient. A first device includes a database storing information identifying chemical compounds of an averse food ingredient and identifying chemical compounds of a flavorful food ingredient, and a processor for calculating a food additive such that an olfactory perception of flavors of a mixture of the averse food ingredient, the flavorful food ingredient and the food additive is (Continued)

the same as an olfactory perception of only the flavorful food ingredient.

20 Claims, 4 Drawing Sheets

(58) Field of Classification Search
USPC ...... 73/19.06, 19.05, 37, 19.01, 23.2, 23.34; 702/19, 22, 23, 27, 179, 183
See application file for complete search history.

(56) References Cited

U.S. PATENT DOCUMENTS

| | | | |
|---|---|---|---|
| 6,077,318 A * | 6/2000 | Trinh | A61L 9/01 252/8.91 |
| 6,248,135 B1 | 6/2001 | Trinh et al. | |
| 7,222,634 B2 * | 5/2007 | Hess | A01M 31/025 135/901 |
| 2002/0142477 A1 * | 10/2002 | Lewis | G01N 33/0031 436/151 |
| 2005/0048186 A1 * | 3/2005 | Lehmberg | A23F 3/38 426/594 |
| 2007/0111251 A1 * | 5/2007 | Rosania | C40B 30/06 435/7.1 |
| 2009/0311403 A1 * | 12/2009 | Grab | A21D 13/08 426/535 |
| 2010/0248390 A1 * | 9/2010 | Matsunami | G01N 33/566 436/501 |
| 2010/0265059 A1 * | 10/2010 | Melker | G08B 21/245 340/539.11 |
| 2015/0066386 A1 * | 3/2015 | Varshney | G01N 33/0001 702/23 |

OTHER PUBLICATIONS

Young, J., "Making Sense of Scents," Bowhunting World, Apr. 25, 2011, http://www.grandviewoutdoors.com/articles/making-sense-of-scents#sthash.co69SuJg.dpbs.

G.M. Shephard, "Smell Images and the flavor system in the human brain," Nature, vol. 444, No. 7117, pp. 316-321, Nov. 2006.

Y.-Y. Ahn, S. E. Ahnert, J.P. Bagrow, and A.-L. Barabasi, "Flavor Network and the principles of food pairing," Sci. Reports, vol. 1, p. 196, Dec. 2011.

I. D. Fisk, A. Kettle, S. Hofmeister, A. Virdie, and J. S. Kenny, "Discrimination of Roast and Ground Coffee Aroma," Flavour Journal, vol. 1, No. 14, pp. 1-8, 2012.

T. Weiss, K. Snitz, A. Yablonka, R. M. Khan, D. Gafsou, E. Schneigman, N. Sobel, "Perceptual Convergence of multi-component mixtures in olfactory implies an olfactory white," PNAS, vol. 109, No. 49, Dec. 2012.

R. M. Khan, C.-H. Luk, A. Flinker, A. Aggarwal, H. Lapid, R. Haddad, N. Sobel, "Predicting Odor Pleasantness from Odorant Structure: Pleasantness as a Reflection of the Physical World," The Journal of Neuroscience, vol. 27, No. 37, Sep. 2007.

A. A. Koulakov, B. E. Kolterman, A. G. Enikolopov, D. Rinberg, "In Search of the Structure of Human Olfactory Space," Frontiers in Neuroscience, vol. 5, No. 65, pp. 1-8, Sep. 2011.

* cited by examiner

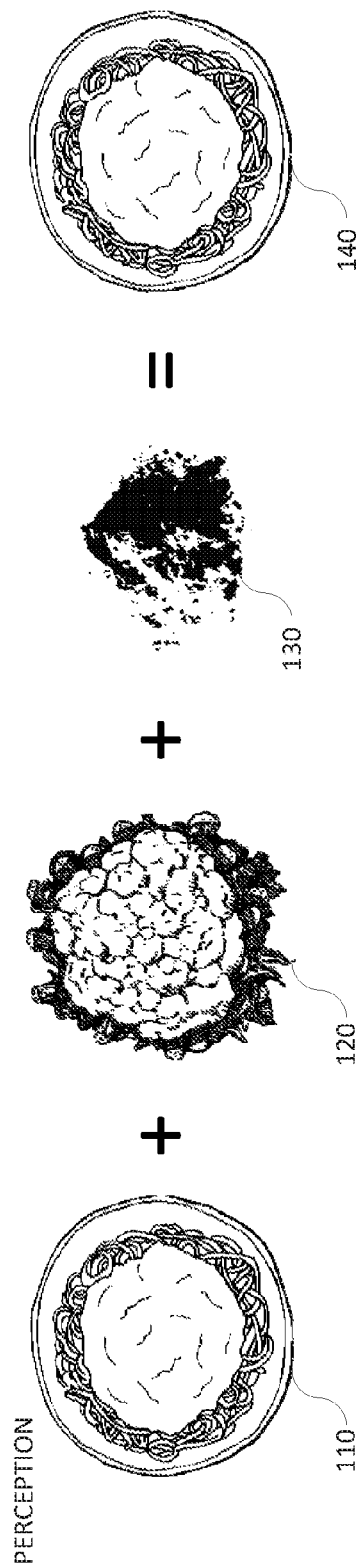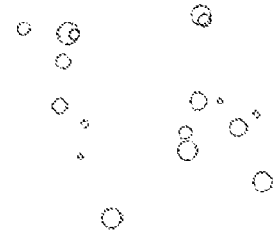
FIG. 1
FIG. 2

FOOD STEGANOGRAPHY

FIELD OF THE DISCLOSURE

This disclosure relates generally to the field of food preparation, and more specifically to altering the flavor perception of food using flavoring compounds.

BACKGROUND OF THE DISCLOSURE

Human flavor perception is complicated, involving a variety of external sensory stimuli and internal states. Not only does it involve the five classical senses, but also sensing through the gut, and the emotional, memory-related, motivational, and linguistic aspects of food. First, there are the basic tastes: sweet, sour, salty, bitter, and umami. The smell of foods is the key contributor to flavor perception, which is in turn a property of the chemical compounds contained in the ingredients. There are typically tens to hundreds of different flavor compounds per food ingredient.

In addition, many children, as well as adults, are picky eaters. Most children eat a wide variety of foods until they are around two years old, when they suddenly stop. The phase can last until a child is four or five years of age. It is believed to be an evolutionary response. Toddlers' taste buds shut down at about the time they start walking, giving them more control over what they eat. However, junk food such as ice cream, French fries and soda are often more attractive to the eater than healthy foods such as brown rice and broccoli. This is also believed to be an evolutionary instinct useful when humans used to wander around in the woods searching for food. In the distant past, humans depended heavily on their senses to make a decision of what to eat and what not to eat. In nature, foods that are sweet are almost always safe to eat and are nutritious. They make hunger go away; foods that smell odd, or taste bitter or sour usually mean they are potentially toxic or spoiled, and less safe to eat. In the modern environment, where food is bought in supermarkets or restaurants, those same survival instincts often serve instead to make humans obese and chronically ill.

SUMMARY OF THE DISCLOSURE

In one embodiment, the present disclosure is a method for calculating a food additive. For example, the method includes identifying chemical compounds of an averse food ingredient, identifying chemical compounds of a flavorful food ingredient and calculating a set of chemical compounds for the food additive such that an olfactory perception of a mixture of the averse food ingredient, the flavorful food ingredient and the food additive is the same as an olfactory perception of only the flavorful food ingredient.

In another embodiment, the present disclosure is an additional method for calculating a food additive. The method includes identifying chemical compounds of an averse food ingredient, identifying chemical compounds of a flavorful food ingredient, determining a set of physicochemical properties of the chemical compounds of the averse food ingredient and calculating physicochemical properties for the food additive such that an olfactory perception of a mixture of the averse food ingredient, the flavorful food ingredient and the food additive is the same as an olfactory perception of only the flavorful food ingredient. The method further includes selecting chemical compounds for the food additive, wherein, when the chemical compounds that are selected are mixed to form the food additive, the food additive comprises the physicochemical properties that are calculated for the food additive.

In another embodiment, the present disclosure is a further method for calculating a food additive. The method includes generating a projection of a combination of a flavorful food ingredient, an averse food ingredient and a food additive in a perceptual space, wherein the projection comprises a first vector in the perceptual space. The method next includes generating a projection of the flavorful food ingredient in the perceptual space, wherein the projection of the flavorful food ingredient in the perceptual space comprises a second vector in the perceptual space. The method then selects the food additive such that a difference between the first vector and second vector is minimized.

In another embodiment, the present disclosure is a device that includes a database storing information identifying chemical compounds of an averse food ingredient and identifying chemical compounds of a flavorful food ingredient, and a processor for calculating a food additive such that an olfactory perception of flavors of a mixture of the averse food ingredient, the flavorful food ingredient and the food additive is the same as an olfactory perception of only the flavorful food ingredient.

In another embodiment, the present disclosure is a system that includes a gas chromatography apparatus, a processor and a compound mixer. The gas chromatography apparatus is for identifying chemical compounds of an averse food ingredient and for identifying chemical compounds of a flavorful food ingredient. The processor is for calculating a food additive such that an olfactory perception of a mixture of the averse food ingredient, the flavorful food ingredient and the food additive is the same as an olfactory perception of only the flavorful food ingredient. The compound mixer is for mixing flavor compounds to create the food additive.

In still another embodiment, the present disclosure is a device that include a processor and a computer-readable medium storing instructions, which when executed by the processor, cause the processor to perform operations. The operations include identifying chemical compounds of an averse food ingredient, identifying chemical compounds of a flavorful food ingredient and calculating a set of chemical compounds for the food additive such that an olfactory perception of a mixture of the averse food ingredient, the flavorful food ingredient and the food additive is the same as an olfactory perception of only the flavorful food ingredient.

BRIEF DESCRIPTION OF THE DRAWINGS

The teachings of the present disclosure can be readily understood by considering the following detailed description in conjunction with the accompanying drawings, in which:

FIG. 1 illustrates a conceptual representation of an embodiment of the present disclosure;

FIG. 2 illustrates a graph of olfactory/flavor physicochemical space reduced to two principal component dimensions, according to the present disclosure;

DETAILED DESCRIPTION

Figure 3:
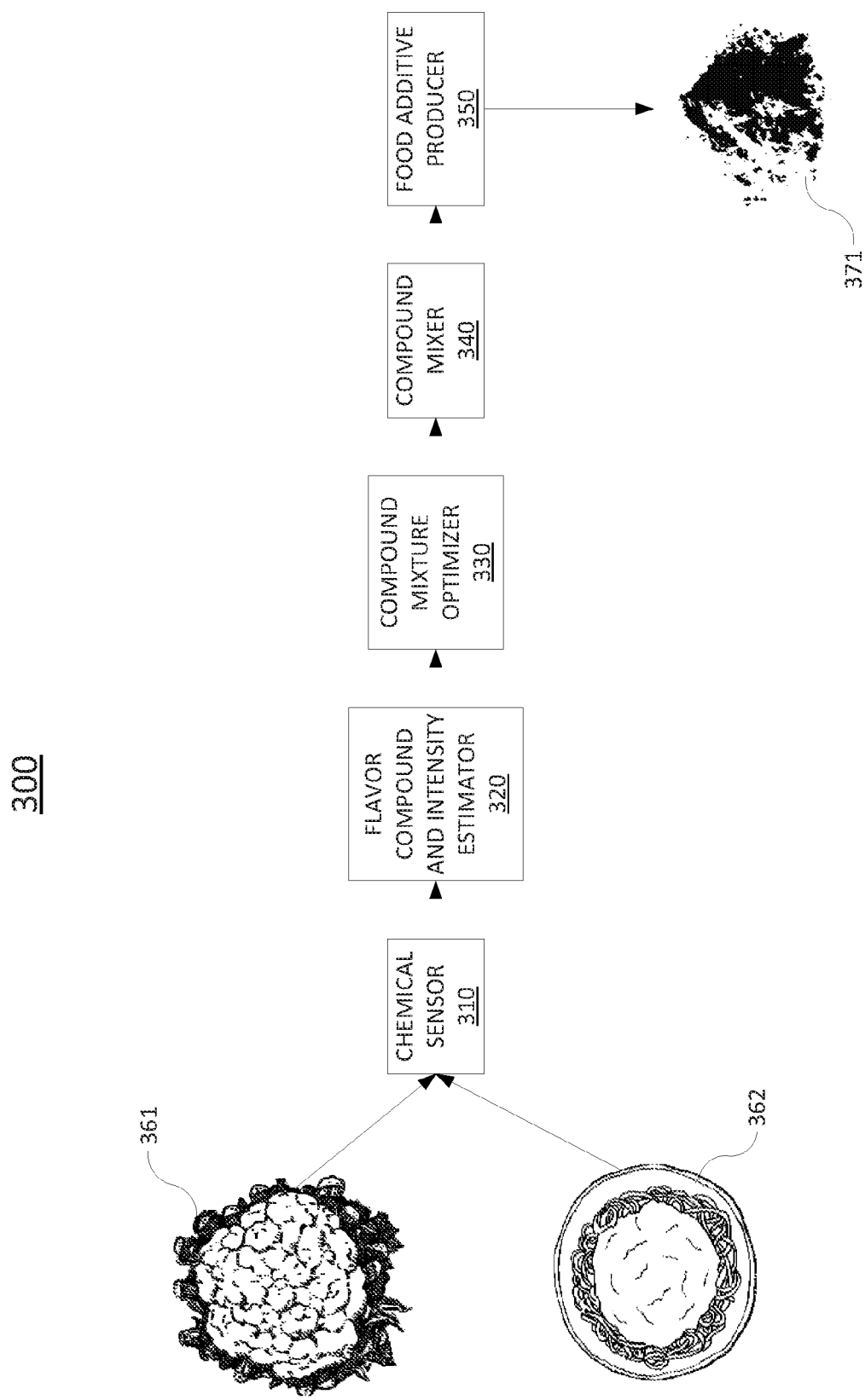
FIG. 3 is a high-level block diagram of an exemplary system for calculating and producing a food additive, according to the present disclosure.

The present disclosure is directed to several problems relating to the palatability of nutritious foods. For example, some people and animals are averse to the flavor of certain foods that have nutritional benefit. It is much easier to get those people or animals to eat foods they find flavorful. If an averse food (e.g., a nutritious food) can be hidden inside a flavorful food, then it will be easier to feed those people or animals with those foods. However, human flavor perception is complicated, involving a variety of external sensory stimuli and internal states. For example, the smell of foods is the key contributor to flavor perception, which is in turn a property of the chemical compounds contained in the ingredient. However, there are typically tens to hundreds of different chemical compounds contributing to flavor and smell per food ingredient.

Embodiments of the present disclosure aim to increase the palatability of an averse food (that is, a nutritious food that may have a generally undesirable flavor perception) by using the concept of "flavor whiteness" to actively sense and estimate the flavor composition of the averse food and at least one flavorful food, and then to find an optimal set of flavor compounds to produce a food additive to mix with the two foods such that only the flavor of the flavorful food is perceived when consumed in a mixture. Conceptually, the present disclosure can be described as a food steganography process that hides the flavor of an unpleasant or averse food.

Steganography is the science of hiding information. Whereas the goal of cryptography is to make data unreadable by a third party, the goal of steganography is to hide the data. There are a large number of familiar steganographic methods: invisible ink and microdots, secreting a hidden message in the second letter of each word of a large body of text, spread spectrum radio communication, etc. The following formula provides a generic description of the steganographic process: cover_medium+hidden_data+stego_key=stego_medium. The process of the present disclosure comprises using a flavorful food as the cover medium, the averse food as the hidden data and the food additive that is produced as the steganographic key, which are combined to produce a resulting food composition, the "steganographic medium." FIG. 1, illustrates a conceptual representation 100 of an embodiment the present disclosure. In particular, representation 100 illustrates the combining of a flavorful food 110 (e.g., macaroni and cheese) with an averse food 120 (e.g., cauliflower) and a calculated food additive 130 such that in the resulting food dish 140, only the flavorful food is perceived.

Flavor whiteness is a concept relating to flavor perception that has analogs within other sensory fields. For example, in the area of visual perception, two mixtures, each containing an independent set of many different wavelengths, may produce a common color percept termed "white." In the realm of auditory perception, or "audition," two mixtures, each containing an independent set of many different frequencies, may produce "white noise." Visual and auditory whites emerge upon two conditions: when the mixture components span stimulus space, and when they are of equal intensity. Similarly, at least one study has shown that similar conditions apply to odorant mixtures which can be merged to produce an "olfactory white". For example, Weiss, et al. in "Perceptual convergence of multi-component mixtures in olfaction implies an olfactory white," Proceedings of the National Academy of Sciences of the United States of America, vol. 109, no. 49, pp. 19959-19964, Dec. 4, 2012, shows experimentally that mixtures of approximately 30 or more olfactory components which have features that span the stimulus space and which are of relatively equal intensity lead to a common olfactory perception, which has been termed olfactory white. Notably, mixtures of entirely different components that do not overlap or only partially overlap nevertheless can lead to the same perception of olfactory white.

Since the smell of foods is the key contributor to flavor, an olfactory white implies that a flavor white also exists. However, the stimulus space for olfactory perception, and therefore for flavor perception, is far more complicated than the analogs for visual and auditory perception. For example, for visual and auditory perception, there are well defined ranges of frequencies/wavelengths and magnitudes of signals that can be perceived by humans. Thus, each of these modes of perception essentially comprise a single dimension (frequency/wavelength of light and frequency/wavelength of sound waves, respectively). On the other hand, there is not a singular aspect to the perception of smell (and flavor). Rather, olfactory perception and flavor perception includes a vast number of dimensions.

For example, the olfactory perceptual space may include a hyper/multidimensional space that may include up to 146 or more perceptual labels/descriptors (e.g., 146 dimensions) which may include the well known descriptors: fruity, floral, fragrant, soapy, sweet, sulfurous, yeasty, and so forth. Each one of these descriptors (dimensions) may have a different intensity weight for a different food ingredient and for different common isolated chemical compounds that may be found in foods and fragrances. Thus, in the perceptual space, each food ingredient or chemical compound may be represented as a vector in X dimensions, where X is a number of available perceptual descriptors, wherein each perceptual descriptor occupies a different dimension, and where a value of the vector in each dimension relates to a perceived intensity of the food ingredient or chemical compound with respect to that particular descriptor.

It should be noted that the present disclosure may in some instances describe olfactory perceptual and physicochemical spaces, and in other instances describe flavor perceptual and physicochemical spaces. However, insofar as smell is the primary contributor to flavor, the olfactory and flavor spaces may be considered interchangeably for purposes of the present disclosure. In addition, it is noted that more than 100 common chemical compounds in foods and fragrances have been quantified in the olfactory perceptual space, e.g., using human test subjects to rate and quantify perceptions of the isolated chemical compounds. In other words, at the very least, these compounds have known vector representations in the perceptual space. However, there is a vastly greater number, more than 1000 known compounds, commonly used for olfaction and flavor research and which are known to contribute to smell and/or flavor perception. As an example, one particular cheese may have more than 600 of these unique chemical compounds contained therein in different amounts. Similarly, cauliflower may have more than 70 unique compounds contained therein in different amounts.

In addition, a food and/or chemical compound present in the food can be represented as a vector based upon one or more physicochemical or physical descriptors in a physicochemical space. For example, the physicochemical space may have more than 1500 dimensions relating to the molecular properties of different chemical compounds, of which approximately only 40-50 are considered statistically relevant to olfaction and/or flavor. These physicochemical properties include: the molecule's polarity, a number of bonds, a number of hydrogen atoms, a number of heavy atoms, presence and quantity of esters (e.g., monoesters, diesters, triesters, etc.), aldehydes and/or ketones, a length of ester sidechain, and so forth. Thus, each chemical compound can be represented as a vector in the physicochemical space based upon its molecular properties. For example, a compound with 7 bonds and 5 hydrogen atoms and that is a diester may comprise a vector of [7, 5, 2] in the dimensions of "number of bonds" and "number of hydrogen atoms" and "number of ester groups." It should be noted that the present disclosure considers that olfactory perception (and flavor perception) correlates to features of molecules, rather than the identities of the molecules.

In one example, the perceptual space may comprise up to 146 dimensions, while the physicochemical space may comprise more than 1500 dimensions (or between 40 and 50 dimensions if limited to those considered most relevant to olfaction). However, each of the physicochemical and perceptual spaces may be collapsed into hyper/multidimensional spaces with a smaller number of dimensions. For example, any one or more dimensions in the full perceptual space may be collapsed into a lesser number of "principal component" dimensions, each principal component dimension including from one to several of the original dimensions. For example, a multidimensional space may be collapsed into a two-dimensional space having a first dimension, principal component 1, and a second dimension, principal component 2. In addition, in principal component analysis (PCA), different dimensions are selected for aggregation with one another such that in the resulting space with a reduced number of dimensions, a maximum variability in the data set is captured given the available number of dimensions in the reduced-dimensional space. Note that the principal component dimensions are orthogonal to one another. Thus, the features represented by each of the principal component dimensions remain orthogonal to one another.

Vectors in a hyper-dimensional space can similarly be collapsed to a lesser-dimensional vector by collapsing each of its constituent components in each of the collapsed dimensions. As just one example, FIG. 2 illustrates an exemplary graph 200 of the physicochemical space reduced to two principal component dimensions (PC1 and PC2). For instance, the points illustrated on the graph 200 may represent the principal component vectors of different chemical compounds contained in a flavorful food, such as macaroni and cheese. In one example, the physicochemical and/or the perceptual space is normed such that different dimensions, relating to different properties which are not necessarily of the same type, are scaled accordingly.

With respect to the olfactory perceptual space, it has been shown that only two principal component dimensions capture greater than 50 percent of the variance of known chemicals in the original 146-dimensional space. With only approximately 10 dimensions, nearly 90 percent of the variation can be retained. Similarly, it has been shown that the first two principal component dimensions in the physicochemical space may account for more than 40 percent of the entire variance in the physicochemical space, while the first 10 principal component dimensions can account for 70 percent of the variation.

In addition to the above, the perceptual space is known to generally correspond to the physicochemical space. In other words, attributes in the perceptual space can be predicted from attributes in the physicochemical space, and vice versa. In particular, more than 100 common compounds have been quantified in the perceptual space. Further, since the molecular properties of these chemicals are also known, a generalized correspondence between particular physicochemical properties in the physicochemical space and perceptual descriptors and magnitudes the perceptual space has been derived from this rich set of data. For example, it has been shown that with a two-dimensional perceptual space and a two-dimensional physicochemical space created by principal component analysis (PCA), there is a strong correlation between a first principal component dimension in the perceptual space and a first principal component dimension in the physicochemical space and a similarly strong correlation between a second principal component dimension in the perceptual space and a second principal component dimension in the physicochemical space.

It should be noted that these exemplary principal component dimensions are not observable in the real world and cannot be experienced and perceived as such. However, to provide some frame of reference, the perceptual descriptors most strongly associated with the first principal component dimension in the perceptual space may include fragrant/sweet at the one extreme and putrid/rancid at the other extreme, while the second principal component dimension is associated with the descriptors of ether/gasoline at one extreme and smoky/woody at the other extreme. Similarly, in the two-dimensional physicochemical space, the first principal component dimension may be most strongly associated with hydrophobicity and polarity while the second principal component dimension may be strongly associated with a number of carbon atoms, among other physicochemical properties.

The foregoing example describes the correlation between the first two principal component dimensions in the perceptual space and the first two principal component dimensions in the physicochemical space. This is perhaps the most important and the most useful statistical correlation between the perceptual and physicochemical spaces. However, it should be noted that the use of further correlations based upon individual physicochemical properties may also be employed by embodiments of the present disclosure. For example, the length of side-chains of dipeptide esters has been correlated to the degree of sweetness. Thus, a mathematical correspondence between the ester side-chain length of a compound (e.g., a dimension in the physicochemical space) and the sweetness and/or fruitiness (e.g., a single dimension, or two dimensions in the perceptual space) may be inferred.

As further isolated chemical components are quantified in the perceptual space, more accurate correlations between other physicochemical properties (physicochemical dimensions) and other perceptual descriptors (perceptual dimensions) can be inferred. The same framework can be extended to derive correspondences between the physicochemical space and the perceptual space for various additional chemical compounds that share similar features with the more than 100 chemical compounds that have previously been quantified in the perceptual space. In any case, a vector representation of a chemical compound in the perceptual space is associated with an analogous vector representation of the compound in the physicochemical space whether explicitly (e.g., for the at least 100 chemical compounds that have been quantified experimentally in the perceptual space) or by inference as described above (e.g., using the essentially direct correlation between the two-dimensional perceptual space and the two-dimensional physicochemical space).

To further aid in understanding the present disclosure, FIG. 3 illustrates an exemplary system 300 for calculating an optimal food additive for steganographic combining with at least one averse food and at least one flavorful food. In particular, the system 300 includes five principal components: chemical sensor 310, flavor compound and intensity estimator 320, compound mixture optimizer 330, compound mixer 340 and food additive producer 350. The system 300 accepts as inputs at least one averse food 361, e.g., cauliflower, and at least one flavorful food 362, e.g., macaroni and cheese, which are analyzed by chemical sensor 310. It should be noted that as used herein the terms averse food and flavorful food are broadly applicable to different classes and types of foods as they may be perceived by any one or more individuals. Thus, for example, one person may find a particular food to be undesirable or averse, while another person may enjoy the same food and consider it to be desirable, tasty and flavorful. As such, embodiments of the present disclosure are broadly applicable to the hiding of one food with another food using a flavor additive that is determined in accordance with the systems, devices and methods described herein. Accordingly, the term "averse food" is broadly applicable to any food which is to be "hidden," and the term "flavorful food" is broadly applicable to any food which is used as a cover medium to hide the averse food.

In one embodiment, chemical sensor 310 is for detecting chemical components of both the at least one averse food 361 and the at least one flavorful food 362. For example, the chemical sensor/intensity estimator 310 may detect more than 70 individual chemical components of cauliflower and more than 600 individual chemical components of cheese, along with the quantities and/or percentages by weight of each component within each of the foods. In one embodiment, the chemical sensor 310 uses gas chromatography, which may include mass-spectrometry, photo-ionization detection, and the like, to determine the components that are present and their overall and/or relative quantities. Accordingly, chemical sensor 310 may comprise or may be part of a gas chromatography apparatus, as is known to those skilled in the art. It should be noted that in many instances, well-known foods have already been profiled in this manner. As such, in one embodiment the system 300 may simply obtain a chemical profiles of the at least one averse food 361 and/or the at least one flavorful food 362, e.g., as stored data. Thus, in one example, chemical sensor 310 may be considered an optional part of the system.

The next component of system 300 is the flavor compound and intensity estimator 320, which determines the chemical compounds that are deemed to most strongly contribute to the olfactory perception and flavor of the at least one averse food 361 and the at least one flavorful food 362. For instance, as mentioned above, a particular cheese may include more than 600 different chemical compounds. However, many of the 600 chemical compounds may only be present in trace amounts. In addition, many of the 600 chemical compounds may be known to have little or no impact on flavor (and olfactory) perception, whereas other ones of the 600 chemical compounds may be known to have a strong contribution to the flavor (and olfactory) perception. In any case, the flavor compound and intensity estimator 320 may obtain this information from the chemical sensor 310 and/or from stored data relating to common foods.

As also mentioned above, each chemical compound of a food ingredient can be represented in the physicochemical space as a vector based directly upon known physical and/or chemical features of the chemical compound, e.g., number of bonds, number of carbon atoms, hydrophobicity, number of hydrogen atoms, length of ester sidechains, quantities of ester groups, alkyl groups and ketone groups, and so forth.

As such, the flavor compound and intensity estimator 320 may select the top X and/or Y chemical compounds of the at least one averse food 361 and/or the at least one flavorful food 362 and determine their physicochemical vectors. From these selected sets of vectors in the physicochemical space, the flavor compound and intensity estimator 320 may then translate or project the selected set of vectors for each of the at least one averse food 361 and/or the at least one flavorful food 362 to respective vectors in the flavor perceptual space.

It should be noted that in another embodiment, a projection of a food (in aggregate) may be known. For example, flavor/olfactory perception scores for macaroni and cheese (as opposed to flavor perception scores for the pure, individual chemical compounds contained therein) may have been created or may be created via flavor perception surveys. In this case, a vector in the perceptual space for macaroni and cheese need not be derived via projection of its constituent chemicals from the physicochemical space to the perceptual space.

Compound mixture optimizer 330 is tasked with calculating an optimal food additive 371 to be added with the at least one averse food 361 and the at least one flavorful food 362 such that when a food dish comprising the mixture of the three is consumed, the person eating the mixture will only perceive the flavorful food. Accordingly, the compound mixture optimizer performs such calculations over the flavor perceptual space. However, this task may lead to an unbounded solution set (an essentially infinite number of solutions). As such, compound mixture optimizer 330 calculates at least one optimal solution to the problem. For instance, in one embodiment, the optimizer 300 may find a "lowest cost" or a low cost solution. In one embodiment, the lowest cost solution may be constrained by the availability or non-availability of certain compounds, the cost of such compounds, the relative nutrition or lack thereof of certain compounds, and so forth.

Once the optimal food additive 371 is calculated, compound mixer 340 may obtain and mix the desired quantities of the compounds that are calculated. In addition, food additive producer 350 may further process the mixture to place it in a form that is suitable for inclusion in food and/or for human consumption. It should be noted that in one example, the flavor compound and intensity estimator 320 and compound mixture optimizer 330 may comprise a single device rather than separate devices or modules. As an example, the flavor compound and intensity estimator 320 and compound mixture optimizer 330 may be embodied as a single computing device, such as general purpose computing device 500 of FIG. 5.

In one embodiment, the calculations made by compound mixture optimizer 330 may be implemented as follows:

$\Re_+^n$ represents a non-negative real space of flavor compound quantities. For example, n is the number of available chemical compounds (there are more than 1000 known and typically used for flavor/olfactory research).

g, h, a $\in \Re_+^n$ are flavor compound vectors for the flavorful food, the averse food and the optimal compound mixture respectively. For example, g is a vector comprising the chemical compounds and the amounts present in the flavorful food, h is a vector comprising the chemical compounds and the amounts present in the flavorful food and a is a vector comprised of a plurality of chemical compounds to be computed and their amounts.

P is a projection from $\Re_+^n$ to $\Re^d$ where d<n such that $\Re^d$ is a normed flavor perceptual space of d dimensions. It should be noted that g, h and a can be mapped into the physicochemical space as respective sets of vectors in the physicochemical space, which may then be mapped into the perceptual space as respective vectors in the perceptual space.

$w \in \Re^d$ represents olfactory (and flavor) white (it is a vector in the perceptual space).

One way to represent the optimization problem for the compound mixture optimizer 330 is:

$$\min_a \|P(g+h+a) - P(g) - w\| \quad \text{(Equation 1)}$$

where $P(g+h+a)$ is a vector in the perceptual space that corresponds to the set of vectors in the physicochemical space for the collective chemical components from all of the flavorful food, the averse food and the flavor additive. $P(g)$ is a vector in the perceptual space that corresponds to the perception of the flavorful food alone (e.g., macaroni and cheese). Thus, $P(g)$ may be projected from the set of vectors representing macroni and cheese in the physicochemical space.

It is noted that the minimization problem of Equation 1 has an unbounded solution set. Thus, the problem can be restated as:

$$\min_a \|P(g+h+a) - P(g) - w\| + \lambda J(a) \quad \text{(Equation 2)}$$

where λ is a scalar and J(a) is a regularization term that is a function of vector a and which may incorporate objectives such as finding the solution with the minimum norm (including sparsity), minimum monetary cost, maximizing lifetime of compound mixer 340 by evenly using available constituent chemicals, minimizing the use of certain types of chemical compounds (e.g., minimizing the inclusion of alcohols, artificial flavors and the like), minimizing the quantity or size of compounds to be added, and other optimality principles.

It should be noted that in Equations 1 and 2, the problem attempts to find a vector a such that $P(g+h+a)$ is as close to $P(g)$ as possible. In other words, select a set of compounds and select the amounts of each compound to mix into a food additive such that the perception of a food dish comprising the flavorful food, the averse food and the food additive tastes and/or smells as close to the taste/flavor of the flavorful food as possible. Note that the optimization problem includes a perceptual space vector for olfactory flavor white, vector w. The need to include w in the optimization problem arises from the fact that flavor and smell are not subtractive. In other words, there are no flavors or smells which negate each other in the sense that some sound or light waves may cancel each other out to form a null or zero. Thus, olfactory white is not a true "zero" point, but has some positive perception. As such, w is included in the optimization problem as a normalization term.

It is also noted, however, that there is not a single olfactory/flavor white. Instead, many different combinations of approximately 30 or greater chemical compounds having features that span the stimulus space and which are of relatively equal intensity can be considered to be olfactory/flavor white. Accordingly, in one example the projection of these different olfactory/flavor white chemical compound combinations in the perceptual space may be set as: $W \subset \Re^d$. In this example, the optimization problem becomes:

$$\min_a \min_{w \in W} \|P(g+h+a) - P(g) - w\| + \lambda J(a) \quad \text{(Equation 3)}$$

where the goal is to find a vector, a, such that $P(g+h+a)$ is as close to $P(g)$ as possible, but where a range of different possible olfactory/flavor whites $w \in W$, may be used. For instance, any combination of approximately 30 or more chemical compounds having features that span the feature space and which have relatively equal intensities comprises an olfactory white.

Figure 4:
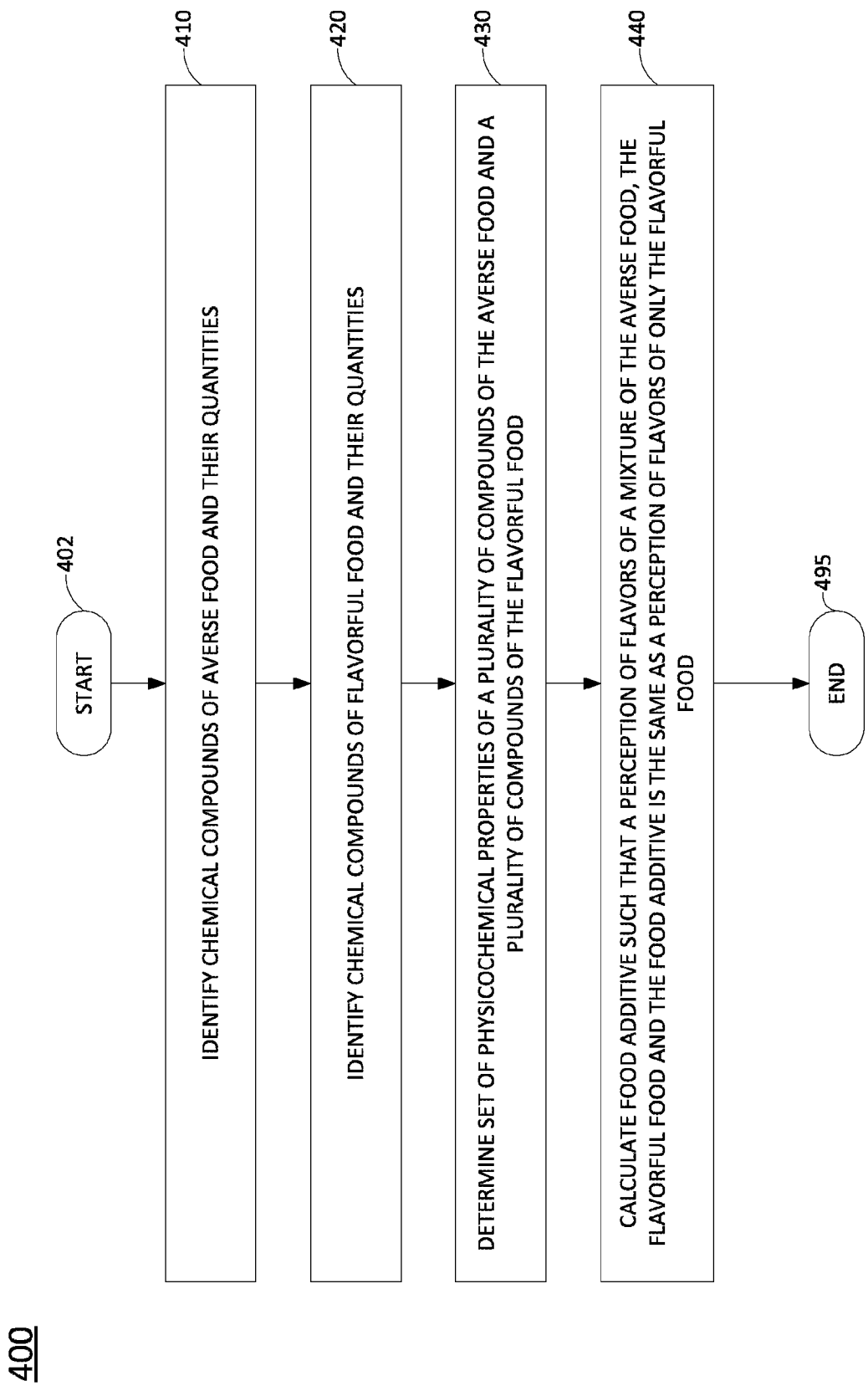
FIG. 4 is a flow diagram of an exemplary method for calculating a food additive, according to the present disclosure.

FIG. 4 is a flow diagram illustrating one embodiment of a method 400 for calculating a food additive. More specifically, the method 400 is for steganographic combining of an averse food, a flavorful food and an optimal food additive comprising an mixture of flavor compounds such that when the combination is consumed, only the flavor and/or smell of the flavorful food is perceived. In one example, any one or more steps, functions and/or operations of the method 400 may be implemented by any one or more components of the system 300 in FIG. 3. Alternatively, or in addition, any one or more steps, functions and/or operations of the method 400 by may be performed by a computing device 500 and/or a processor of such a computing device as described in connection with FIG. 5 below. For illustrative purposes, the method 400 is described below in connection with this particular example.

The method 400 begins at step 402 and proceeds to step 410 where the processor identifies chemical compounds of at least one averse food (broadly, an averse food ingredient) and their quantities. For example, in one embodiment a gas chromatography apparatus may be used to sense the chemical compounds that constitute the at least one averse food and to determine the weights and/or relative amounts present in the at least one averse food. more than 70 unique chemical compounds may be found in cauliflower in this manner. In another embodiment, at step 410 the processor obtains data regarding the chemical compounds and their amounts present in the at least one averse food from a database/data store, e.g., from any one or more of an attached memory, an external database accessed over a network, a disk drive, and the like. For instance, a database may be embodied in a storage device, such as storage device 506 in FIG. 5, discussed below.

In step 420, the processor identifies chemical compounds of at least one flavorful food (broadly, at least one flavorful food ingredient) and their quantities. In one embodiment, a gas chromatography apparatus may be used to sense the chemical compounds of the at least one flavorful food and to determine their relative weights and/or relative amounts present in the at least one flavorful food. For example, gas chromatography may determine that a flavorful food such as macaroni and cheese is composed of more than 600 unique chemical compounds. In another embodiment, at step 420 the processor obtains data regarding the chemical compounds and their amounts present in the at least one flavorful food from a data store, e.g., from any one or more of an attached memory, an external database accessed over a network, a disk drive, and the like.

In step 430, the processor determines a set of physicochemical properties of a plurality of chemical compounds of the at least one averse food and a plurality of chemical compounds of at least one flavorful food. For instance, as described above, cauliflower (an averse food in this example) and macaroni and cheese (a flavorful food in this example) may be comprised of more than 70 and 600 chemical compounds respectively. However, although the number of chemical compounds present may be relatively large, it is by and large known which compounds contribute to smell and flavor and which have little effect in the olfactory/flavor perceptual space. As such, certain compounds may be excluded from further analysis and processing at step 430, allowing the processor to focus on only the most important compounds. In addition, certain compounds may be present in such trace amounts that they may also be ignored and/or excluded from further processing at step 430, since these compounds also contribute little to the overall flavor and smell of the food. Accordingly, step 430 may involve selecting only a portion of the chemical compounds present in either or both of the at least one averse food and the at least one flavorful food.

In any case, once the chemical compounds of the at least one averse food and the at least one flavorful food are known, relevant physicochemical properties of each of the compounds may readily be determined. For example, there are more than 1000 well known chemical compounds that are used in olfactory and flavor research and which are known to contribute to smell and/or flavor. In addition, the physicochemical properties of these compounds are also well known such that, once a particular chemical compound is identified, it can be correlated to its physicochemical properties. For example, the identities of flavor compounds and their physicochemical properties may be stored in a list or database such that the properties can simply be looked-up and indexed by chemical compound name/identity.

In one embodiment, at step 430 the processor may create a vector in the physicochemical space for each of a plurality of chemical compounds selected for either or both of the at least one averse food and the at least one flavorful food. For instance, the processor may determine a vector for each compound in a multi-dimensional physicochemical space, where each dimension corresponds to a particular physicochemical property. Alternatively, or in addition, the processor may create a vector for each chemical compound in a lesser dimensional, "normed" space having principal component dimensions which may comprise linear projections of two or more dimensions aggregated with one another, wherein each principal component dimension is orthogonal to the other principal component dimensions, and where the principal component dimensions are selected to maintain a maximum variance in the data set given the resulting number of dimensions in the reduced-dimensional space. In any case, at step 430 the processor may create in the physicochemical space a set of vectors for the plurality of chemical compounds of the averse food and a set of vectors for the plurality of chemical compounds flavorful food.

At step 440, the method 400 calculates a food additive such that when the at least one flavorful food, the at least one averse food and the flavor additive are mixed into a single food dish and consumed, only the flavorful food is perceived. For example, the processor may solve an optimization problem, e.g., based upon Equations 1, 2 or 3 above. For instance, the processor may determine a minimum cost vector comprising a plurality of flavor compounds and their relative quantities, using any of these equations. In one embodiment, the optimization problem involves finding a vector a such that $P(g+h+a)$ is as close to $P(g)$ as possible, where $P(g)$ is a projection (vector) in the perceptual space representing the perception of the at least one flavorful food and $P(g+h+a)$ is a projection (vector) in the perceptual space representing the aggregate/combined perception of the at least of flavorful food, g, the at least one averse food, h, and the flavor additive, a, mixed together in one food dish.

In one embodiment, vector a is calculated based upon a correlation between the perceptual space and the physicochemical space. In other words, desirable perceptual qualities and relative intensities that are necessary to bring $P(g+h+a)$ into similarity $P(g)$ are determined in the perceptual space, which are then capable of reverse-projection into desirable physicochemical properties in the physicochemical space. For example, with a two-dimensional perceptual space and a two-dimensional physicochemical space created by principal component analysis (PCA), there is a strong correlation between a first principal component dimension in the perceptual space and a first principal component dimension in the physicochemical space and a similarly strong correlation between a second principal component dimensions in the perceptual space and a second principal component dimension in the physicochemical space. Accordingly, at step 440 these and other known connections between perceptual descriptors and intensities and physicochemical properties may be used to reverse-project into the physicochemical space. In other words, desirable physicochemical properties (which may be represented by a vector in the physicochemical space) maybe identified by reverse-projecting from the perceptual space into the physicochemical space.

Accordingly, in one embodiment, at step 440, the processor calculates a food additive comprising a set of flavor compounds such that when mixed together, the food additive has these desirable physicochemical properties. It is noted that as stated, this task has practically an infinite number of solutions. For instance, as mentioned above a database may include a list of known chemical compounds and their physicochemical properties, such that chemical compounds that satisfy the criteria of the optimization problem can be determined by matching desirable physicochemical properties of the food additive determined at step 440 with physicochemical properties of the different chemical compounds listed in the database. However, in the realm of available chemical compounds there exist numerous different individual chemical compounds which may satisfy one or more aspects of the particular physicochemical criteria determined at step 440. Thus, in one example, at step 440 the processor further calculates the food additive under certain constraints, such as minimizing the cost of the food additive based upon the costs of the different available chemical components or calculating the food additive components where certain chemical compounds may not be available or may be disfavored (e.g., alcohols, artificial versus naturally derived chemical components, and so forth). In one example, these optimization criteria/constraints are represented by the term $\lambda J(a)$ in Equations 2 and 3 above.

In one embodiment, at step 440, the processor further performs the calculation of the food additive while normalizing the optimization problem to an olfactory white. It is noted that olfactory white arises when approximately 30 or more chemical compounds are present and have features spanning the stimulus space with relatively equal intensity. Since olfactory white is anon-zero concept, the minimization of the distance between the projection of the at least one flavorful food and the projection of the aggregate food dish (the combination of the at least of flavorful food, the at least one averse food and the flavor additive mixed together in one food dish) is normalized to the vector of an olfactory white in the perceptual space.

It is also noted that there are many possible olfactory whites. Thus, in one embodiment step 440 involves finding a lowest cost solution using any available olfactory white (e.g., a lowest cost and/or closest-distance olfactory white).

In other words, the particular lowest cost solution that is found at step 440 may be affected by external criteria, such as described above, e.g. $\lambda J(a)$, which may comprise a preference for naturally derived flavor compounds, or less expensive or more readily available flavor compounds, as well as by the distance to a closest olfactory white vector. This particular example is captured in Equation 3 above.

In one embodiment, at step 440 the processor further outputs the composition of the food additive that is calculated. For example, the processor may output a recommendation for a food additive comprising a mixture of any number of different chemical compounds (e.g., 5-15 different compounds). It is noted that olfactory white arises when approximately 30 or more chemical compounds are present and have features spanning the stimulus space with relatively equal intensity. However, since the food additive is being combined with the compounds that are already present in the at least one averse food and the at least one flavorful food, the necessary spanning of the stimulus space will often be achievable with a food additive having substantially less than 30 chemical compounds.

Following step 440, the method 400 proceeds to step 495 where the method ends.

It should be noted that in various embodiments, any one or more of steps 410-440 of the method 400 may be performed in a different order that that which is illustrated herein. Similarly, any one or more of steps 410-440 may be considered to be optional steps, and may therefore be omitted without departing from the scope of the present disclosure. In addition, although not expressly specified above, one or more steps, functions or operations of method 400 may include a storing, displaying and/or outputting step as required for a particular application. In other words, any data, records, fields, and/or intermediate results discussed in the method can be stored, displayed and/or outputted to another device as required for a particular application. Furthermore, steps or blocks in FIG. 4 that recite a determining operation or involve a decision do not necessarily require that both branches of the determining operation be practiced. In other words, one of the branches of the determining operation can be deemed as an optional step.

Figure 5:
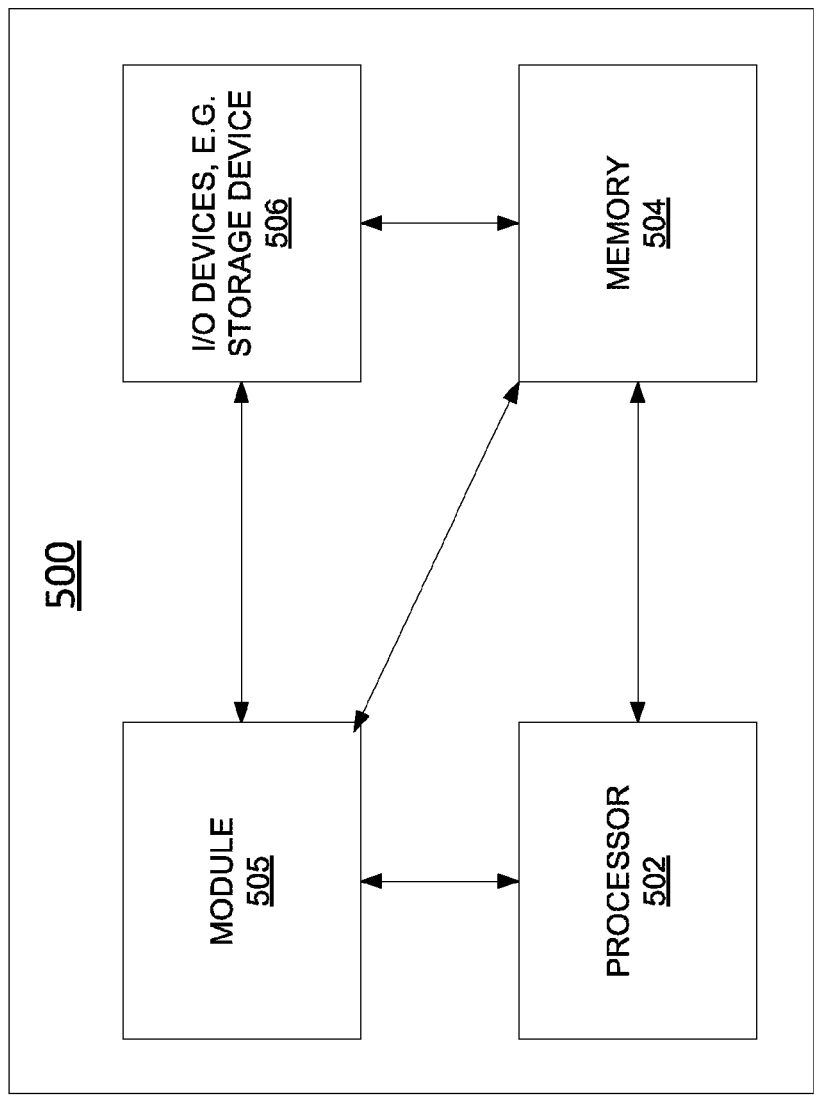
FIG. 5 is a high-level block diagram of a general purpose computing device suitable for use in performing the functions described herein.

FIG. 5 is a high-level block diagram of a general purpose computing device 500 suitable for use in performing the steps, functions and operations described herein. In one embodiment, general purpose computing device 500 comprises a processor 502, a memory 504, a module 505 for calculating a food additive and various input/output (I/O) devices 506 such as a display, a keyboard, a mouse, a stylus, a wireless network access card, an Ethernet interface, and the like. In one embodiment, at least one I/O device is a storage device (e.g., a disk drive, an optical disk drive, a floppy disk drive). It should be understood that the module 405 can be implemented as a physical device or subsystem that is coupled to a processor through a communication channel.

Alternatively, the module 405 for calculating a food additive can be represented by one or more software applications (or even a combination of software and hardware, e.g., using Application Specific Integrated Circuits (ASIC)), where the software is loaded from a storage medium (e.g., I/O devices 506) and operated by the processor 502 in the memory 504 of the general purpose computing device 500. Thus, in one embodiment, the module 505 for calculating a food additive, as described herein with reference to the preceding figures, can be stored on a tangible (e.g., non-transitory) computer readable storage medium (e.g., RAM, magnetic or optical drive or diskette, and the like).

While the foregoing is directed to embodiments of the present invention, other and further embodiments of the invention may be devised without departing from the basic scope thereof. Various embodiments presented herein, or portions thereof, may be combined to create further embodiments.

What is claimed is:

1. A method, comprising:
    identifying a first set of chemical compounds contained in an averse food ingredient;
    identifying a second set of chemical compounds contained in a flavorful food ingredient, different from the averse food ingredient;
    formulating a new, third set of chemical compounds, different from the first set of chemical compounds and the second set of chemical compounds, by selecting individual chemical compounds to combine in the third set of chemical compounds and by selecting defined quantities for each of the individual chemical compounds,
    wherein when the individual chemical compounds are mixed in the defined quantities, they produce a food additive such that an olfactory perception of a mixture of the averse food ingredient, the flavorful food ingredient and the food additive is the same as an olfactory perception of only the flavorful food ingredient.

2. The method of claim 1, wherein the formulating comprises:
    minimizing a difference between a vector projection of the mixture of the averse food ingredient, the flavorful food ingredient, and the food additive in a perceptual space with a vector projection of the flavorful food in the perceptual space.

3. The method of claim 2, wherein the minimizing the difference comprises normalizing a solution to a vector representation of an olfactory white in the perceptual space.

4. The method of claim 2, wherein the perceptual space comprises a multidimensional space where each dimension is associated with a different olfactory or flavor perceptual descriptor.

5. The method of claim 2, the perceptual space comprises a multidimensional space where at least one dimension is associated with at least two different olfactory or flavor perceptual descriptors.

6. The method of claim 2, wherein the formulating comprises determining a set of physicochemical properties for the food additive, where the determining the set of physicochemical properties for the food additive is based upon at least one correlation between the perceptual space and a physicochemical space.

7. The method of claim 1, wherein the formulating comprises:
    calculating a set of physicochemical properties for the food additive such that the olfactory perception of the mixture of the averse food ingredient, the flavorful food ingredient, and the food additive is the same as the olfactory perception of only the flavorful food ingredient.

8. The method of claim 7, wherein the individual chemical compounds are selected such that, when the individual chemical compounds are combined in the defined quantities, the food additive comprises the set of physicochemical properties that is calculated for the food additive.

9. The method of claim 1, wherein the identifying the first set of chemical compounds of the averse food ingredient comprises sensing chemical compounds in the averse food ingredient by gas chromatography, and wherein the identifying the second set of chemical compounds of the flavorful food ingredient comprises sensing chemical compounds in the flavorful food by gas chromatography.

10. The method of claim 1, wherein the individual chemical compounds in the third set of chemical compounds are selected based at least in part upon an availability of one or more of the individual chemical compounds in the third set of chemical compounds or such that a cost of the third set of chemical compounds is minimized.

11. The method of claim 1, further comprising:
determining a first set of physicochemical properties of the first set of chemical compounds of the averse food ingredient; and
determining a second set of physicochemical properties of the second set of chemical compounds of the flavorful food ingredient.

12. The method of claim 11, wherein the determining the first set of physicochemical properties of the first set of chemical compounds of the averse food ingredient comprises performing a database lookup to match the first set of chemical compounds of the averse food ingredient with their respective physicochemical properties, and wherein the determining the second set of physicochemical properties of the second set of chemical compounds of the flavorful food ingredient comprises performing a database lookup to match the second set of chemical compounds of the flavorful food ingredient with their respective physicochemical properties.

13. The method of claim 11, further comprising:
determining a first set of vectors in a physicochemical space based upon the first set of physicochemical properties of the first set of chemical compounds of the averse food ingredient; and
determining a second set of vectors in the physicochemical space based upon the second set of physicochemical properties of the second set of chemical compounds of the flavorful food ingredient.

14. The method of claim 13, wherein the physicochemical space comprises a multidimensional space where each dimensions is associated with a different physicochemical property.

15. The method of claim 13, wherein the physicochemical space comprises a normed multidimensional space where at least one dimension is associated with at least two different physicochemical properties.

16. The method of claim 13, further comprising:
calculating a first vector projection associated with the mixture of the averse food ingredient, the flavorful food ingredient, and the food additive in a perceptual space, wherein the calculating the first vector projection is based on the first set of vectors in the physicochemical space and the second set of vectors in the physicochemical space; and
calculating a second vector projection associated with the flavorful food in the perceptual space, wherein the second vector projection is based on the second set of vectors in the physicochemical space.

17. The method of claim 1, further comprising:
obtaining the individual chemical compounds in the third set of chemical compounds in the defined quantities; and
mixing the individual chemical compounds in the defined quantities to produce the food additive in a form that is suitable for human consumption.

18. A method, comprising:
identifying a first set of chemical compounds contained in an averse food ingredient;
identifying a second set of chemical compounds contained in a flavorful food ingredient;
determining a first set of physicochemical properties of the first set of chemical compounds of the averse food ingredient;
determining a second set of physicochemical properties of the second set of chemical compounds of the flavorful food ingredient;
calculating a third set of target physicochemical properties for a food additive such that an olfactory perception of a mixture of the averse food ingredient, the flavorful food ingredient, and the food additive is the same as an olfactory perception of only the flavorful food ingredient; and
formulating the food additive by selecting individual chemical compounds to include in a new, third set of chemical compounds, different from the first set of chemical compounds and the second set of chemical compounds, and by selecting defined quantities in which to mix the individual chemical compounds in the third set of chemical compounds,
wherein when the individual chemical compounds are mixed in the defined quantities, they produce a food additive whose physicochemical properties match the third set of target physicochemical properties.

19. The method of claim 18, wherein the calculating the third set of target physicochemical properties for the food additive comprises:
minimizing a difference between a vector projection of the mixture of the averse food ingredient, the flavorful food ingredient, and the food additive in a perceptual space with a vector projection of the flavorful food in the perceptual space.

20. The method of claim 19, wherein the minimizing the difference comprises normalizing a solution to a vector representation of an olfactory white in the perceptual space.

* * * * *